United States Patent
Park et al.

[11] Patent Number: 5,916,995
[45] Date of Patent: Jun. 29, 1999

[54] ACETAL-SUBSTITUTED AROMATIC HYDROXY COMPOUNDS AND NEGATIVE PHOTORESIST COMPOSITIONS COMPRISING THE SAME

[75] Inventors: Joo-Hyeon Park; Seong-Ju Kim; Ji-Hong Kim; Sun-Yi Park, all of Taejeon, Rep. of Korea

[73] Assignee: Korea Kumho Petrochemical Co., Ltd., Seoul, Rep. of Korea

[21] Appl. No.: 08/932,358

[22] Filed: Sep. 17, 1997

[30] Foreign Application Priority Data

Sep. 21, 1996 [KR] Rep. of Korea .................. 96-41436

[51] Int. Cl.$^6$ .................................................. C08G 59/00
[52] U.S. Cl. ........................... 528/104; 528/100; 528/86; 528/403; 528/425; 525/333.3; 549/357; 549/430
[58] Field of Search ..................... 528/104, 100, 528/86, 403, 425; 525/333.3; 549/357, 430

[56] References Cited

FOREIGN PATENT DOCUMENTS 10182537  7/1998  Japan .

*Primary Examiner*—Duc Truong
*Attorney, Agent, or Firm*—Harrison & Egbert

[57] ABSTRACT

There are disclosed an aromatic hydroxy compound or polymer substituted with acetal of Formula (I), (II) or (III), and a negative photoresist composition prepared therefrom. The pattern formed of the negative photoresist composition has good cross sections in addition to being superior in transmissivity to deep uv light and excimer laser and in thermal resistance and storage stability after exposure.

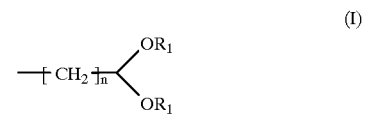

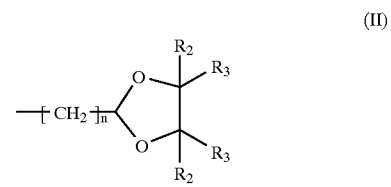

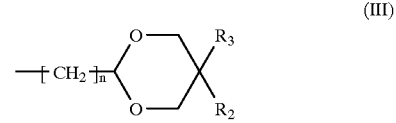

1 Claim, No Drawings

ACETAL-SUBSTITUTED AROMATIC HYDROXY COMPOUNDS AND NEGATIVE PHOTORESIST COMPOSITIONS COMPRISING THE SAME

BACKGROUND OF THE INVENTION

1. Field of the invention

The present invention relates to aromatic hydroxy compounds or polymers substituted with acetal group(s) and a negative photoresist compositions containing the same.

2. Description of the Prior Art

The high integration of semiconductor devices has always been followed by significant advance in lithography. For example, ultra-fine patterns as small as sub-microns or quarter-microns in size must be required for the fabrication of ultra-LSI. Accordingly, the light sources used to form the fine patterns become shorter in wavelength from g-line to i-line and deep uv light, further to excimer laser, such as KrF laser, and finally to electron beams.

Since the photoresists prepared from conventional novolak-quinone diazides used for g-line or i-line show large absorption peaks at the wavelength range of deep uv light and excimer laser, a fine pattern cannot be obtained from the photoresists. Thus, there was a strong demand for a material which little absorbs the light belonging to such wavelength ranges. In response to the demand, active research has been directed to the development of chemical amplified photoresists based on polyhydroxystyrene derivatives which are smaller in absorption than novolak-quinonediazides.

Chemical amplified photoresists consist mainly of a base resin and a compound which generates acid upon radiation (hereinafter referred to as "photoacid generator"). Depending whether the photoacid acts to increase or decrease the solubility of the base resin, the chemical amplified photoresist is classified into positive or negative resist. The former is one which increase in solubility, the latter decreasing in solubility.

For example, U.S. Pat. No. 4,491,628 discloses a positive photoresist employing as a base resin polyhydroxystyrene whose hydroxy groups are partly replaced with t-butylcarboxy groups. A negative photoresist employs polyhydroxystyrene in combination with hexamethoxymethylmelamine as a crosslinking agent, as disclosed in Proc. SPIE, 1466, 246, 1991.

However, there is a significant disadvantage in such conventional positive and negative resists each: for positive resist, patterns are developed into a T shape by the amine in the air: for negative resist, as the methanol which is produced as a by-product upon crosslinking is escaped from the patterns formed, they undergo a considerable change in volume.

SUMMARY OF THE INVENTION

The present inventors repeated to develop novel photoresist polymers through the intensive and thorough research, in order to overcome the above problems. As a result, they found that, if some acetal group(s) is bonded to aromatic hydroxy compounds or polymers, the compounds or polymer can be used to prepare photoresists which little undergo the volume change upon pattern formation and show high sensitivity and resolution in addition to being transparent to deep uv light and excimer laser. Further experiments showed that the photoresists prepared from the acetal-substituted aromatic hydroxy compounds or polymers were superior in thermal resistance and storage stability after exposure.

Therefore, it is an object of the present invention to provide an aromatic hydroxy compound or polymer at least one hydroxy group of which is substituted by an acetal group.

It is another object of the present invention to provide a negative photoresist composition comprising said aromatic hydroxy compound, which is useful to form fine patterns suitable for the high integration of semiconductor devices.

In accordance with an aspect of the present invention, there is provided an aromatic hydroxy compound or polymer substituted by at least one selected from the acetal groups represented by the following formulas (I), (II) and (III):

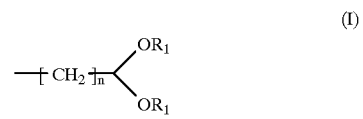

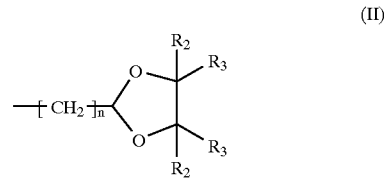

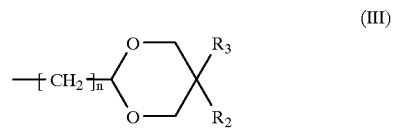

wherein n is an integer of 1–6; $R_1$ is an alkyl group, a phenyl group or a benzyl group; $R_2$ and $R_3$ are independently represented by a hydrogen atom, an alkyl group, a phenyl group or a benzyl group.

In accordance with another aspect of the present invention, there is provided a negative photoresist composition comprising the aromatic hydroxy compound, an alkali-soluble resin and a photoacid generator.

In accordance with a further aspect of the present invention, there is provided a negative photoresist composition comprising the aromatic hydroxy polymer and a photoacid generator.

DETAILED DESCRIPTION OF THE INVENTION

The present invention pertains to an aromatic hydroxy compound useful to give a chemical amplified negative photoresist composition, represented by the following general formula (IV-1), (IV-2), (IV-3) or (IV-4):

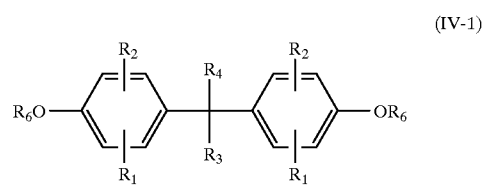

-continued

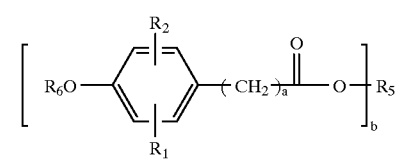
(IV-2)

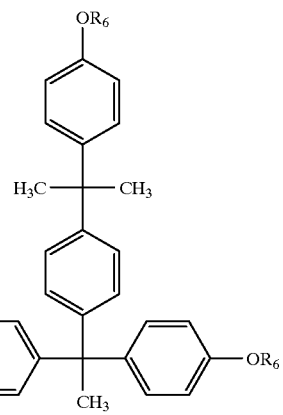
(IV-3)

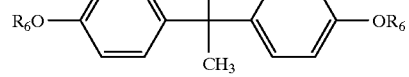

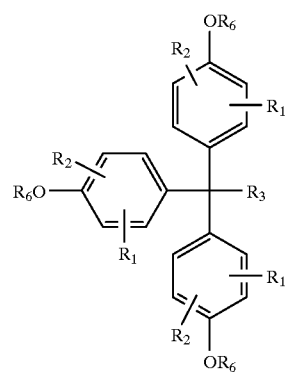
(IV-4)

wherein a is an integer of 0–5; b is an integer of 2–4; $R_1$ and $R_2$ are independently represented by a hydrogen atom, an alkyl group, an alkoxy group, a phenyl group or a halogen atom; $R_3$ and $R_4$ are independently represented by a hydrogen atom, an alkyl group or a phenyl group; $R_5$ is a carbon atom, an alkyl group, an alkyl group containing hydroxy, or an alkyl group containing phenyl; and $R_6$ is a hydrogen atom or an acetal group selected from the following formulas (I), (II) and (III) with a proviso that at least one $R_6$ is the acetal group:

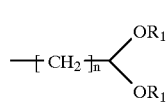
(I)

-continued (II)

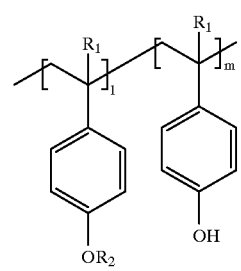

(III)

wherein n is an integer of 1–6; $R_1$ is an alkyl group, a phenyl group or a benzyl group; $R_2$ and $R_3$ are independently represented by a hydrogen atom, an alkyl group, a phenyl group or a benzyl group, and to a polymer for chemical amplified negative photoresist composition, represented by the following general formula (V):

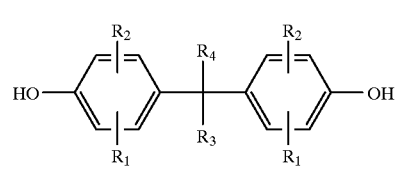
(V)

wherein l and m each represent a mole ratio, satisfying the condition of l+m=1; $R_1$ is a hydrogen atom or a methyl group; $R_2$ is an acetal group of Formula (I), (II) or (III).

As for the aromatic hydroxy compounds, it is preferable a phenol derivative which contains at least two hydroxy groups. As a monomer, the aromatic hydroxy compound is represented by the following formula (VI):

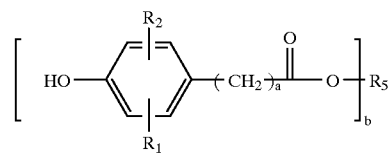
(VI-1)

(VI-2)

-continued

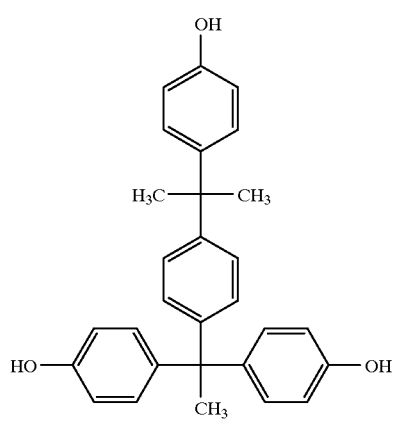
(VI-3)

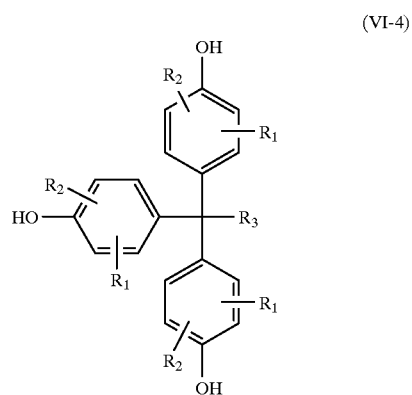
(VI-4)

wherein a is an integer of 0–5; b is an integer of 2–4; $R_1$ and $R_2$ are independently represented by a hydrogen atom, an alkyl group, an alkoxy group, a phenyl group or a halogen atom; $R_3$ and $R_4$ are independently represented by a hydrogen atom, an alkyl group or a phenyl group; and $R_5$ is a carbon atom, an alkyl group, an alkyl group containing hydroxy, or an alkyl group containing phenyl. As a polymer, the aromatic hydroxy compound is an alkali-soluble resin represented by the following formula (VII):

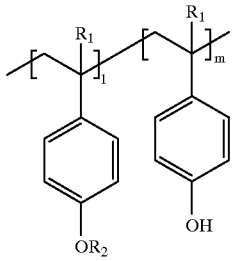
(VII)

wherein 1 and m each represent a mole ratio, satisfying the condition of 1+m=1; and $R_1$ is a hydrogen atom or a methyl group. Preferable examples of the aromatic hydroxy compound include polyhydroxystyrene and novolak resins.

When hydroxy groups in the alkali-soluble resin are substituted with an acetal group, the hydroxy groups of the resin can be substituted at an amount of 1–99 mole %. In accordance with the present invention, preferable is the alkali-soluble resin in which the hydroxy groups are substituted by the acetal groups of Formula (I), (II) or (III) at an amount of 5–40 mole %. For example, if the substitution occurs at greater amounts, the resulting negative photoresist shows a reduced solubility in an aqueous alkali solution at its un-exposed regions. However, even in this case, this problem can be overcome by adding the aromatic hydroxy compound itself as an additive.

When the aromatic hydroxy monomer of Formula (VI) is used for the preparation of a negative photoresist composition, the hydrogens of its hydroxy groups may be, fully or partially, substituted by the compounds of Formula (I), (II) or (III). If partially substituted aromatic hydroxy monomer is used, the resulting resist is advantageous in that the storage stability of resist is improved and the un-exposed regions have an increased solubility to aqueous basic solution.

The substitution with the compound of Formula (I), (II) or (III) can be accomplished by the reaction of the aromatic hydroxy compound with an acetal-containing alkyl halide compound in the presence of a basic catalyst. Examples of the basic catalyst include sodium hydroxide, potassium hydroxide, lithium hydroxide, tetraalkylammonium hydroxide and tertially amine. This reaction may be carried out in a solvent, which is exemplified by alcohols, acetonitriles, dimethylacetamides, dimethylform amide, dioxanes, and tetrahydrofuran. Depending, in part, on the base catalyst, the reaction temperature ranges preferably from about 60 to 150° C. Thus, an example of this reaction may be represented as follows:

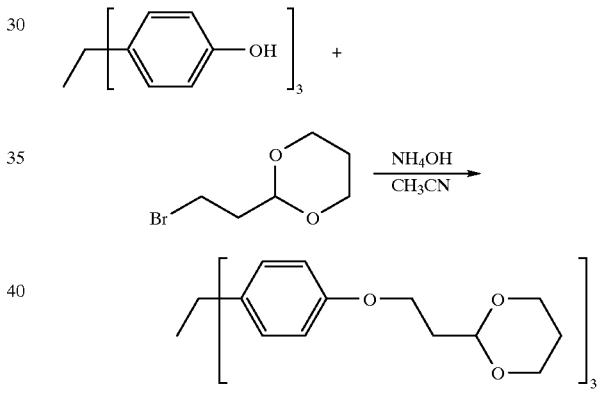

In accordance with the present invention, there is provided a two-component system photoresist which comprises a photoacid generator and an alkali-soluble base resin substituted with the functional group of Formula (I), (II) or (III). Optionally, to this two-component system resist may be added an aromatic hydroxy compound as an additive in order to increase the solubility of the un-exposed regions in alkali. This additive may be either a polymer resin or an aromatic hydroxy monomer which is dissolved in aqueous alkali solution. The additive is preferably added to the photoresist composition at an amount of about 5–50 weight parts based on 100 weight parts of the base resin. In the two-component system, the resin used ranges, in polystyrene-reduced average molecular weight, from about 1,000 to 1,000,000 and preferably from 2,000 to 30,000.

In accordance with the present invention, there is provided a three-component system photoresist which comprises the aromatic hydroxy compound substituted with the acetal group of Formula (I), (II) or (III), a photoacid generator and a base resin, such as polyhydroxystyrene or novolak resin. The aromatic hydroxy compound is preferably used at an amount of about 10–40 weight parts based on 100 weight parts of the base resin. The polyhydroxystyrene or novolak resin has a polystyrene-reduced average molecular weight of about 1,000–1,000,000.

As the photoacid generator useful for the composition of the present invention may be used well-known one, but not restricted. Specific examples of the photoacid generator include bis(cyclohexylsulfonyl)diazomethane, bis(2,4-dimethylphenylsulfonyl) diazomethane, diphenyliodium tetraflouroborate, diphenyliodonium hexafluorophosphate, diphenyliodonium hexafluoroantimonate, diphenyliodonium trifluoromethane sulfonate (triflate), (4-alkoxyphenyl) phenyliodonium hexafluoroantimonate, (4-alkoxyphenyl) phenyliodonium trifluoromethansulfonate, bis(4-t-butylphenyl)iodonium hexaflourophosphate, bis(4-t-butylphenyl)iodonium hexafluoroantimonate, bis(4-t-butylphenyl)iodonium trifluoromethanesulfonate, bis(4-t-butylphenyl)iodonium tetrafluoroborate, triphenylsulfonium hexafluorophosphate, triphenylsulfonium hexafluoroantimonate, triphenylsulfonium trifluoromethanesulfonate, (4-alkoxyphenyl) phenyl sulfonium hexafluoroantimonate, (4-alkoxyphenyl) henylsulfonium trifluoromethanesulfonate, (4-methylphenyl) diphenylsulfonium trifluoromethanesulfonate, bis(4-methylphenyl)phenylsulfonium trifluoromethanesulfonate, tris(4-methylphenyl)sulfonium trifluoromethanesulfonate, (4-t-butylphenyl)diphenylsulfonium trifluoromethanesulfonate, diphenyl[4-(phenylthio)phenyl] sulfonium hexafluorophosphate, and diphenyl[4-(phenylthio)phenyl]sulfonium hexafluoroantimonate.

The photoacid is used at an amount of about 0.5–15 weight parts and preferably about 1–5 weight parts, based on 100 weight parts of the resin. For example, if the amount of photoacid generator is less, crosslinking reaction proceeds insufficiently. On the other hand, if that is more, fine patterns cannot be obtained because of acid diffusion.

In order to avoid such acid diffusion, basic components may be added to the resist compositions of the present invention. Basic components include bases such as amines, ammonium hydroxides, and sulfonium hydroxides. It is used at an amount of 1–99 mole % of the photoacid generator used in the resist composition and preferably 20–50 mole %.

Upon using the photoresist composition, it is preferred to use it in a solution phase in which the above-mentioned components are dissolved in a solvent. Examples of the solvent include cyclohexanone, 2-hexanone, methylisoamylketone, ethyleneglycol, ethyleneglycol monoacetate, ethylene glycol monomethylether acetate, ethyleneglycol monoethylether acetate, propyleneglycol, propyleneglycol monomethylether, propyleneglycol monoethylether, propyleneglycol monomethylacetate, propyleneglycol monoethylacetate, methyl lactate, ethyl lactate, propyl lactate, methyl formate, ethyl formate, ethyl hydroxyacetate, ethyl 2-hydroxy-2-methylpropionate, methyl 3-methoxy-2-methyl propionate, methyl 2-hydroxy-3-methylbutyrate, ethylmethoxyacetate, ethylethoxyacetate, methyl 3-ethoxypropionate, 3-methoxybutylacetate, 3-methyl-3-methoxybutyl acetate, toluene, xylene, N,N-dimethylformamide, N,N-dimethylacetamide, N-methylpyrrolidone, and gamma-butyrolacetone. They, if necessary, may be used alone or in combination.

To the resist composition of the present invention may be added additives. For example, benzophenones for reducing standing wave, additional resins for improving physical properties of the resulting photoresist, stabilizers, plasticizers, surfactants and/or colorants may be added.

A photoresist film is obtained by coating the photoresist solution on a wafer by appropriate methods such as spin coating, flow coating or roll coating and drying it. If necessary, the photoresist film is pre-baked and then, may be exposed through a mask to a KrF excimer laser light source to form a desired pattern. In order to improve the apparent sensitivity of the resist film, it is preferable to perform a post-baking process. Using a weak-alkali aqueous solution, such as 2.38% tetramethylammoniumhydroxide, a developing process is carried out.

A better understanding of the present invention may be obtained in light of following examples which are set forth to illustrate, but are not to be construed to limit, the present invention.

SYNTHESIS EXAMPLE I

Preparation of Aromatic Hydroxy Compound (IV) Substituted with Acetal Group 26.8 g of tris(4-hydroxyphenyl)ethane was dissolved in 180 ml of acetonitrile in a flask and added with 126 ml of tetramethylammonium hydroxide (25% aqueous solution) and then, with 39.4 ml of 2-(2-bromoethyl)-[1,3]-dioxane. The resulting solution was heated to 80° C. and stirred for 10 hours. The reactant mixture was diluted with 250 ml of ethyl acetate and washed with 300 ml of 5% aqueous sodium hydroxide solution and then, with 300 ml of saline. The organic layer was dried over magnesium sulfate, filtered and deprived of the solvent. The residue was crystallized in methanol, to give 46 g of 1,1,1-tris-[4-(2-[1,3]-dioxan-2-yl ethoxy)phenyl]ethane as a white powder (mp=101° C.), represented by the following formula.

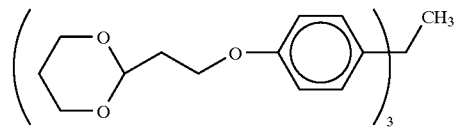

SYNTHESIS EXAMPLE II

Preparation of Aromatic Hydroxy Compound (IV) Substituted with Acetal Group 22.7 g of tris(4-hydroxyphenyl)ethane was dissolved in 150 ml of acetonitrile in a flask and added with 106 ml of tetramethylammonium hydroxide (25% aqueous solution) and then, with 28.7 ml of 2-(2-bromoethyl)-[1,3]-dioxolane. The resulting solution was heated to 80° C. and stirred for 10 hours. The reactant mixture was diluted with 200 ml of ethyl acetate and washed with 300 ml of 5% aqueous sodium hydroxide solution and then, with 300 ml of saline. The organic layer was dried over magnesium sulfate, filtered and deprived of the solvent. Any further filtration was not performed. 40 g of 1,1,1-tris-[4-(2-[1,3]-dioxolan-2-yl ethoxy)phenyl]ethane, represented by the following formula, was obtained in a very viscous form.

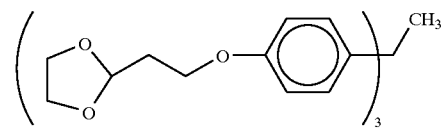

SYNTHESIS EXAMPLE III

A similar procedure to that of Synthesis Example II was repeated except that 28.1 g of bisphenol A, instead of 22.7 g of tris(4-hydroxyphenyl)ethane, and 32.0 ml of 2-(2-bromoethyl)-[1,3]-dioxolane instead of 28.7 ml were used. 48 g of 2,2-bis[4-(2-[1,3]-dioxolan-2-ylethoxy)phenyl] isopropylidene, represented by the following formula, was obtained.

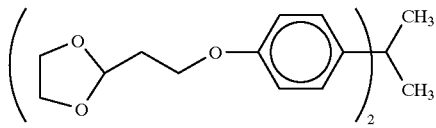

SYNTHESIS EXAMPLE IV

A similar procedure to that of Synthesis Example II was repeated except that 26.3 g of tris(4-hydroxy-3-methylphenyl)ethane, instead of 22.7 g of tris(4-hydroxyphenyl)ethane, and 29.3 ml of 2-(2-bromoethyl)-[1,3]-dioxolane instead of 28.7 ml were used. 43 g of 1,1,1-tris[4-(2-[1,3]-dioxolan-2-yl ethoxy)-3-methylphenyl] ethane, represented by the following formula, was obtained.

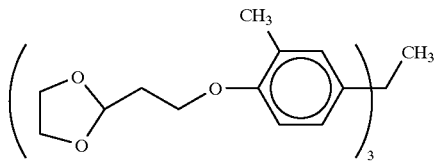

SYNTHESIS EXAMPLE V

Preparation of Aromatic Hydroxy Polymer (V) Substituted with Acetal Group 22.8 g of polyhydroxystyrene (polystyrene-reduced average molecular weight 5,300) was dissolved in 280 ml of ethanol in a flask and added with 140 ml of distilled water and then, with 5.8 ml of 2-(2-bromoethyl)-1,3-dioxane and 12 ml of tetramethylammonium hydroxide (25% aqueous solution). The resulting solution was heated to 80° C. and stirred for 15 hours. After being cooled to room temperature, the reactant mixture was dropwise added to excess distilled water containing 2 g of glacial acetic acid, to give precipitates. They were filtered, dried in vacuo and dissolved in 70 ml of ethyl acetate. This solution was dropwise added to excess toluene to produce precipitates again. These were subjected to filtration and drying, to give 21 g of Resin (A) substituted with acetal. A $^1$H-NMR analysis in which the hydrogen atoms of phenyl group having peaks at 6.2–6.8 ppm were compared with those of the acetal group having a peak at 4.8 ppm, showed that the acetal derivative was substituted at an amount of about 9% in Resin (A).

SYNTHESIS EXAMPLE VI

Preparation of Aromatic Hydroxy Polymer (V) Substituted with Acetal Group 44.2 g of polyhydroxystyrene (polystyrene-reduced average molecular weight 5,300) was dissolved in 550 ml of ethanol in a flask and added with 270 ml of distilled water and then, with 15 ml of 2-(2-bromoethyl)-1,3-dioxane and 31 ml of tetramethylammonium hydroxide (25% aqueous solution). The resulting solution was heated to 80° C. and stirred for 15 hours. After being cooled to room temperature, the reactant mixture was dropwise added to excess distilled water containing 4 g of glacial acetic acid, to give precipitates. They were filtered, dried in vacuo and dissolved in 150 ml of ethyl acetate. This solution was dropwise added to excess toluene to produce precipitates. They were filtered and dried in vacuo to obtain 46 g of Resin(B). It was substituted with the acetal derivative at an amount of 15% as analyzed by $^1$H-NMR.

SYNTHESIS EXAMPLE VII

Preparation of Aromatic Hydroxy Polymer (V) Substituted with Acetal Group 26.5 g of polyhydroxystyrene (polystyrene-reduced average molecular weight 5,300) was dissolved in 330 ml of ethanol in a flask and added with 160 ml of distilled water and then, with 11 ml of 2-(2-bromoethyl)-1,3-dioxane and 23 ml of tetramethylammonium hydroxide (25% aqueous solution). The resulting solution was heated to 80° C. and stirred for 15 hours. After being cooled to room temperature, the reactant mixture was dropwise added to excess distilled water containing 3 g of glacial acetic acid, to give precipitates. They were filtered, dried in vacuo and dissolved in 70 ml of ethylacetate. For precipitation, the solution was dropwise added to excess toluene to produce precipitates. After filtration and drying of the precipitates, 29 g of Resin (C) was obtained. It was substituted with the acetal derivative at an amount of about 19% as analyzed by $^1$H-NMR.

EXAMPLE I 30 weight parts of 1,1,1-tris-[4-(2-[1,3]-dioxolan-ylethoxy)phenyl]ethane obtained in Synthesis Example II, 2.2 weight parts of triphenylsulfonium triflate and 100 weight parts of polyhydroxystyrene (polystyrene-reduced average molecular weight 5,300) were dissolved in 370 weight parts of ethyl lactate. The solution was filtered through a teflon filter having a pore size of about 0.1 μm, to give a photoresist solution. This was coated on a silicon wafer using a spinner and dried at 90° C. for 90 sec to give a resist film 1.0 μm thick. It was exposed through a pattern chrome mask to a KrF excimer laser steper of 248 nm. After the exposure, the wafer was baked at 140° C. for 30 sec.

A developing process was carried out by immersing the wafer in aqueous 2.38 weight % tetramethylammonium hydroxide solution, washing it with deionized water and drying, to prepare a resist pattern. It was found that the line/space negative pattern had a good cross section 0.4 μm thick at an exposure energy of 60 mJ/cm$^2$.

EXAMPLE II

A similar procedure to that of Example I was repeated except that 30 weight parts of 1,1,1-tris-[4-(2-[1,3]-dioxolan-2-yl ethoxy)phenyl]ethane obtained in Synthesis Example II, 3.1 weight parts of triphenylsulfonium triflate, and 18 weight parts of aqueous 1.0 weight % tetramethylammonium hydroxide solution were dissolved in 356 weight parts of ethyl lactate, based on 100 weight parts of polyhydroxystyrene, to prepare a resist solution.

It was found that the line/space negative pattern had a good cross section 0.25 μm thick at an exposure energy of 20 mJ/cm$^2$.

EXAMPLE III

A similar procedure to that of Example I was repeated except that 25 weight parts of 1,1,1-tris-[4-(2-[1,3]-dioxan-2-yl ethoxy)phenyl]ethane obtained in Synthesis Example I, and 2.0 weight parts of triphenylsulfonium triflate were dissolved in 356 weight parts of ethyl lactate, based on 100 weight parts of polyhydroxystyrene, to prepare a resist solution and the wafer was subjected to post-baking at 130° C. for 60 sec.

It was found that the line/space negative pattern had a good cross section 0.4 µm thick at an exposure energy of 60 mJ/cm$^2$.

EXAMPLE IV

A similar procedure to that of Example I was repeated except that 25 weight parts of 1,1,1-tris-[4-(2-[1,3]-dioxan-2-yl ethoxy)phenyl]ethane obtained in Synthesis Example I, 2.8 weight parts of triphenylsulfonium triflate, and 16 weight parts of aqueous 1.0 wt % tetramethyl ammonium hydroxide solution were dissolved in 358 weight parts of ethyl lactate, based on 100 weight parts of Polyhydroxystyrene, to prepare a resist solution and the wafer was subjected to post-baking at 130° C. for 60 sec after exposure.

It was found that the line/space negative pattern had a good cross section 0.3 µm thick at an exposure energy of 40 mJ/cm$^2$.

EXAMPLE V

A similar procedure to that of Example I was repeated except that 2.0 weight parts of triphenylsulfonium triflate was dissolved in 286 weight parts of ethyl lactate, based on 100 weight parts of Resin (A) obtained in Synthesis Example V, to prepare a resist solution and the wafer was subjected to post-baking at 140° C. for 60 sec after exposure.

It was found that the line/space negative pattern had a good cross section 0.5 µm thick at an exposure energy of 80 mJ/cm$^2$.

EXAMPLE VI

A similar procedure to that of Example I was repeated except that 20 weight parts of 1,1,1-tris-[4-(2-[1,3]-dioxan-2-yl ethoxy)phenyl]ethane obtained in Synthesis Example I, 3.0 weight parts of triphenylsulfonium triflate, and 16 weight parts of aqueous 1.0 weight % tetramethylammonium hydroxide were dissolved in 344 weight parts of ethyl lactate, based on 100 weight parts of Resin (A) obtained in Synthesis Example V, to prepare a resist solution and the wafer was subjected to post-baking at 140° C. for 90 sec after exposure.

It was found that the line/space negative pattern had a good cross section 0.3 µm thick at an exposure energy of 60 mJ/cm$^2$.

EXAMPLE VII

A similar procedure to that of Example I was repeated except that 20 weight parts of 1,1,1-tris-[4-(2-[1,3]-dioxolan-2-yl ethoxy)phenyl]ethane obtained in Synthesis Example II, 3.0 weight parts of triphenylsulfonium triflate, and 18 weight parts of aqueous 1.0 weight % tetramethylammonium hydroxide solution were dissolved in 344 weight parts of ethyl lactate, based on 100 weight parts of Resin (A) obtained in Synthesis Example V, to prepare a resist solution and the wafer was subjected to post-baking at 140° C. for 60 sec after exposure.

It was found that the line/space negative pattern had a good cross section 0.22 µm thick at an exposure energy of 20 mJ/cm$^2$.

EXAMPLE VIII

A similar procedure to that of Example I was repeated except that 2.0 weight parts of triphenylsulfonium triflate was dissolved in 286 weight parts of ethyl lactate, based on 100 weight parts of Resin (B) obtained in Synthesis Example VI, to prepare a resist solution and the wafer was subjected to post-baking at 130° C. for 60 sec after exposure.

It was found that the line/space negative pattern had a good cross section 0.5 µm thick at an exposure energy of 60 mJ/cm$^2$.

EXAMPLE IX

A similar procedure to that of Example I was repeated except that 3.0 weight parts of triphenylsulfonium triflate, and 14 weight parts of aqueous 1.0 weight % tetramethylammonium hydroxide solution were dissolved in 288 weight parts of ethyl lactate, based on 100 weight parts of Resin (B) obtained in Synthesis Example VI, to prepare a resist solution and the wafer was subjected to post-baking at 140° C. for 90 sec after exposure.

It was found that the line/space negative pattern had a good cross section 0.45 µm thick at an exposure energy of 60 mJ/cm$^2$.

EXAMPLE X

A similar procedure to that of Example I was repeated except that 15 weight parts of 1,1,1-tris-[4-(2-[1,3]-dioxolan-2-yl ethoxy)phenyl]ethane obtained in Synthesis Example VI, and 2.0 weight parts of triphenylsulfonium triflate were dissolved in 328 weight parts of ethyl lactate, based on 100 weight parts of Resin (B) obtained in Synthesis Example VI, to prepare a resist solution and the wafer was subjected to post-baking at 130° C. for 90 sec after exposure.

It was found that the line/space negative pattern had a good cross section 0.3 µm thick at an exposure energy of 40 mJ/cm$^2$.

EXAMPLE XI

A similar procedure to that of Example I was repeated except that 15 weight parts of 1,1,1-tris-[4-(2-[1,3]-dioxan-2-yl ethoxy)phenyl]ethane obtained in Synthesis Example I, 3.0 weight parts of triphenylsulfonium triflate, and 18 weight parts of aqueous 1.0 weight % tetramethylammonium hydroxide solution were dissolved in 330 weight parts of ethyl lactate, based on 100 weight parts of Resin (B) obtained in Synthesis Example VI, to prepare a resist solution and the wafer was subjected to post-baking at 130° C. for 90 sec after exposure.

It was found that the line/space negative pattern had a good cross section 0.3 µm thick at an exposure energy of 40 mJ/cm$^2$.

EXAMPLE XII

A similar procedure to that of Example I was repeated except that 15 weight parts of 1,1,1-tris-[4-(2-[1,3]-dioxolan-2-yl ethoxy)phenyl]ethane obtained in Synthesis Example II, 3.0 weight parts of triphenylsulfonium triflate, and 16 weight parts of aqueous 1.0 weight % tetramethylammonium hydroxide solution were dissolved in 330 weight parts of ethyl lactate, based on 100 weight parts of Resin (B) obtained in Synthesis Example VI, to prepare a resist solution and the wafer was subjected to post-baking at 140° C. for 90 sec after exposure.

It was found that the line/space negative pattern had a good cross section 0.25 µm thick at an exposure energy of 35 mJ/cm$^2$.

EXAMPLE XIII

A similar procedure to that of Example I was repeated except that 1.5 weight parts of triphenylsulfonium triflate was dissolved in 284 weight parts of ethyl lactate, based on 100 weight parts of Resin (C) obtained in Synthesis Example VII, to prepare a resist solution and the wafer was subjected to post-baking at 130° C. for 40 sec after exposure.

It was found that the line/space negative pattern had a good cross section 0.5 $\mu$m thick at an exposure energy of 80 mJ/cm$^2$.

EXAMPLE XIV

A similar procedure to that of Example I was repeated except that 10 weight parts of 1,1,1-tris-[4-(2-[1,3]-dioxan-2-yl ethoxy)phenyl]ethane obtained in Synthesis Example I, 3.0 weight parts of triphenylsulfonium triflate, and 13 weight parts of aqueous 1.0 weight % tetramethylammonium hydroxide solution were dissolved in 316 weight parts of ethyl lactate, based on 100 weight parts of Resin (C) obtained in Synthesis Example VII to prepare a resist solution and the wafer was subjected to post-baking at 150° C. for 60 sec after exposure.

It was found that the line/space negative pattern had a good cross section 0.3 $\mu$m thick at an exposure energy of 40 mJ/cm$^2$.

EXAMPLE XV

A similar procedure to that of Example I was repeated except that 10 weight parts of 1,1,1-tris-[4-(2-[1,3]-dioxolan-2-yl ethoxy)phenyl]ethane obtained in Synthesis Example II, 3.0 weight parts of triphenylsulfonium triflate, and 15 weight parts of aqueous 1.0 weight % tetramethylammonium hydroxide solution were dissolved in 316 weight parts of ethyl lactate, based on 100 weight parts of Resin (C) obtained in Synthesis VII to prepare a resist solution and the wafer was subjected to post-baking at 150° C. for 60 sec after exposure.

It was found that the line/space negative pattern had a good cross section 0.3 $\mu$m thick at an exposure energy of 40 mJ/cm$^2$.

EXAMPLE XVI

A similar procedure to that of Example I was repeated except that 20 weight parts of 1,1,1-tris-[3-methyl-4-hydroxyphenyl]ethane, 2.2 weight parts of triphenylsulfonium triflate, and 16 weight parts of aqueous 1.0 weight % tetramethylammonium hydroxide solution were dissolved in 342 weight parts of ethyl lactate, based on 100 weight parts of Resin (B) obatained in Synthesis VI, to prepare a resist solution and the wafer was subjected to post-baking at 140° C. for 60 sec after exposure.

It was found that the line/space negative pattern had a good cross section 0.24 $\mu$m thick at an exposure energy of 20 mJ/cm$^2$.

EXAMPLE XVII

A similar procedure to that of Example I was repeated except that 5 weight parts of 1,1,1-tris-[4-(2-[1,3]-dioxan-2-yl ethoxy)phenyl]ethane obtained in Synthesis Example I, 10 weight parts of 1,1,1-tris(3-methyl-4-hydroxyphenyl) ethane, 2.2 weight parts of triphenylsulfonium triflate, and 14 weight parts of aqueous 1.0 weight % tetramethylammonium hydroxide solution were dissolved in 328 weight parts of ethyl lactate, based on 100 weight parts of Resin (B) obtained in Synthesis Example VI, to prepare a resist solution and the wafer was subjected to post-baking at 140° C. for 60 sec after exposure.

It was found that the line/space negative pattern had a good cross section 0.22 $\mu$m thick at an exposure energy of 34 mJ/cm$^2$.

EXAMPLE XVIII

A similar procedure to that of Example I was repeated except that 10 weight parts of 1,1,1-tris-[4-(2-[1,3]-dioxolan-2-yl ethoxy)phenyl]ethane obtained in Synthesis Example II, 10 weight parts of 1,1,1-tris(3-methyl-4-hydroxyphenyl)ethane, 2.2 weight parts of triphenylsulfonium triflate, and 12 weight parts of aqueous 1.0 weight % tetramethylammonium hydroxide solution were dissolved 342 weight parts of ethyl lactate, based on 100 weight parts of Resin (B) obtained in Synthesis Example VI, to prepare a resist solution and the wafer was subjected to post-baking at 140° C. for 60 sec after exposure.

It was found that the line/space negative pattern had a good cross section 0.24 $\mu$m thick at an exposure energy of 20 mJ/cm$^2$.

EXAMPLE XVIIII

A similar procedure to that of Example I was repeated except that 25 weight parts of 2,2-bis[4-(2-[1,3]-dioxolan-2-yl ethoxy)phenyl]isopropylidene obtained in Synthesis Example III, and 2.0 weight parts of triphenylsulfonium triflate were dissolved in 356 weight parts of ethyl lactate, based on 100 weight parts of polyhydroxystyrene, to prepare a resist solution.

It was found that the line/space negative pattern had a good cross section 0.35 $\mu$m thick at an exposure energy of 60 mJ/cm$^2$.

EXAMPLE XX

A similar procedure to that of Example I was repeated except that 25 weight parts of 1,1,1-tris-[4-(2-[1,3]-dioxolan-2-yl ethoxy)-3-methylphenyl]ethane obtained in Synthesis Example IV, and 2.0 weight parts of triphenylsulfonium triflate were dissolved in 356 weight parts of ethyl lactate, based on 100 weight parts of polyhydroxystyrene, to prepare a resist solution.

It was found that the line/space negative pattern had a good cross section 0.40 $\mu$m thick at an exposure energy of 70 mJ/cm$^2$.

EXAMPLE XXI

A similar procedure to that of Example I was repeated except for using 2.5 weight parts of triphenylsulfonium hexafluoroantimonate instead of 2.2 weight parts of triphenylsulfonium triflate.

It was found that the line/space negative pattern had a good cross section 0.40 $\mu$m thick at an exposure energy of 60 mJ/cm$^2$.

As apparent from the above examples, the negative photoresist composition prepared from the aromatic hydroxy compound or polymer substituted with acetal group, in accordance with the present invention, can afford good cross sections when being patterned in addition to being superior in transmissivity to deep uv light and excimer laser and in thermal resistance and storage stability after exposure.

The present invention has been described in an illustrative manner, and it is to be understood the terminology used is intended to be in the nature of description rather than of limitation.

Many modifications and variations of the present invention are possible in light of the above teachings. Therefore, it is to be understood that within the scope of the appended claims, the invention may be practiced otherwise than as specifically described.

What is claimed is:

1. An aromatic hydroxy compound comprising the following general formula (IV-1), (IV-2), (IV-3) or (IV-4):

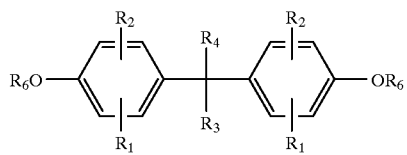
(IV-1)

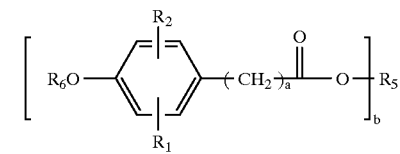
(IV-2)

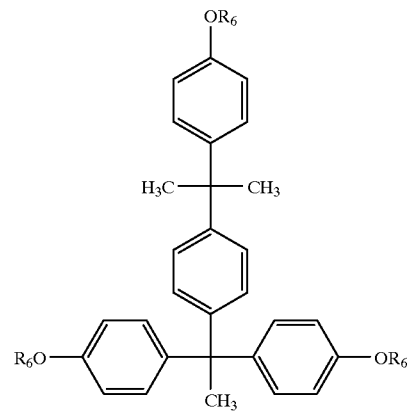
(IV-3)

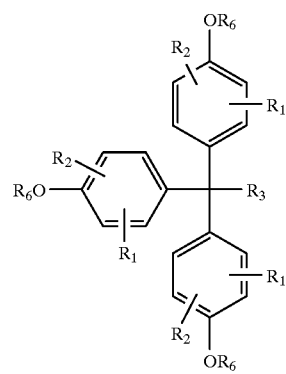
(IV-4)

wherein a is an integer of 0–5; b is an integer of 2–4; $R_1$ and $R_2$ are independently selected from the group consisting of a hydrogen atom, an alkyl group, an alkoxy group, a phenyl group and a halogen atom; $R_3$ and $R_4$ are independently selected from the group consisting of a hydrogen atom, an alkyl group and a phenyl group; $R_5$ is selected from the group consisting of a carbon atom, an alkyl group, an alkyl group containing hydroxy, and an alkyl group containing phenyl; and $R_6$ is a hydrogen atom or an acetal group selected from the following formulas (I), (II) and (III) wherein at least one $R_6$ is the acetal group:

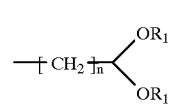
(I)

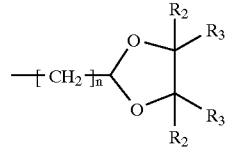
(II)

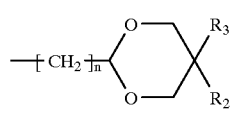
(III)

wherein n is an integer of 1–6; $R_1$ is selected from the group consisting of an alkyl group, a phenyl group and a benzyl group; $R_2$ and $R_3$ are independently selected from the group consisting of a hydrogen atom, an alkyl group, a phenyl group, a benzyl group, and a polymer having the repeating unit of the following formula (V):

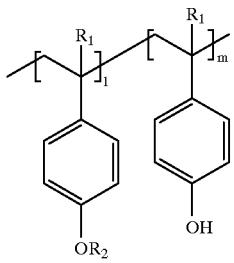
(V)

wherein l and m each represent a mole ratio, satisfying the condition of l+m=1; $R_1$ is selected from the group consisting of a hydrogen atom and a methyl group; $R_2$ is an acetal group of Formula (I), (II) or (III).

* * * * *